United States Patent [19]

Vaillancourt

[11] Patent Number: 4,678,462
[45] Date of Patent: Jul. 7, 1987

[54] STERILE CATHETER SECUREMENT DEVICE

[76] Inventor: Vincent L. Vaillancourt, 14 Bunyan Dr., Livingston, N.J. 07039

[21] Appl. No.: 852,179

[22] Filed: Apr. 15, 1986

[51] Int. Cl.$^4$ .............................................. A61M 25/02
[52] U.S. Cl. .................... 604/180; 128/133; 128/DIG. 26
[58] Field of Search ............ 604/180, 174, 179; 128/DIG. 26, 133, 132

[56] References Cited

U.S. PATENT DOCUMENTS

| | | | |
|---|---|---|---|
| 3,900,026 | 8/1975 | Wagner | 128/133 |
| 3,918,446 | 11/1975 | Buttaravoli | 604/180 X |
| 3,973,565 | 8/1976 | Steer | 604/180 |
| 4,059,105 | 11/1977 | Cutruzzula et al. | 604/18 X |
| 4,122,857 | 10/1978 | Haerr | 604/133 |
| 4,324,237 | 9/1980 | Buttaravoli | 604/180 |
| 4,534,762 | 8/1985 | Heyer | 604/180 |

FOREIGN PATENT DOCUMENTS 2046095  11/1980  United Kingdom ............... 604/180

Primary Examiner—Stephen C. Pellegrino
Attorney, Agent, or Firm—Ralph R. Roberts

[57] ABSTRACT

This invention pertains to the construction and use of a sterile securement device for retaining an inserted and placed catheter and a connected tubular conductor in an assembled condition. This securement device in retaining condition maintains this assembly by this adhesively-coated film which is tightly pressed to the skin of a patient. A frame of sheet material has at least three outer-edge portions providing therebetween a determined interior space or area. This retaining film is a bottom member of film adhesively coated on one side and is attached by the adhesive to one side of this frame. The film within the frame has a flexible release sheet applied to the adhesive surface of this film. An additional protector sheet having a sealable surface is configured to be secured to both the frame and release sheet and has a tab means for removal of this protector and release sheet at time of use. The assembled package is sterilized before shipment and storage. Storage in packages for several devices is contemplated.

34 Claims, 24 Drawing Figures

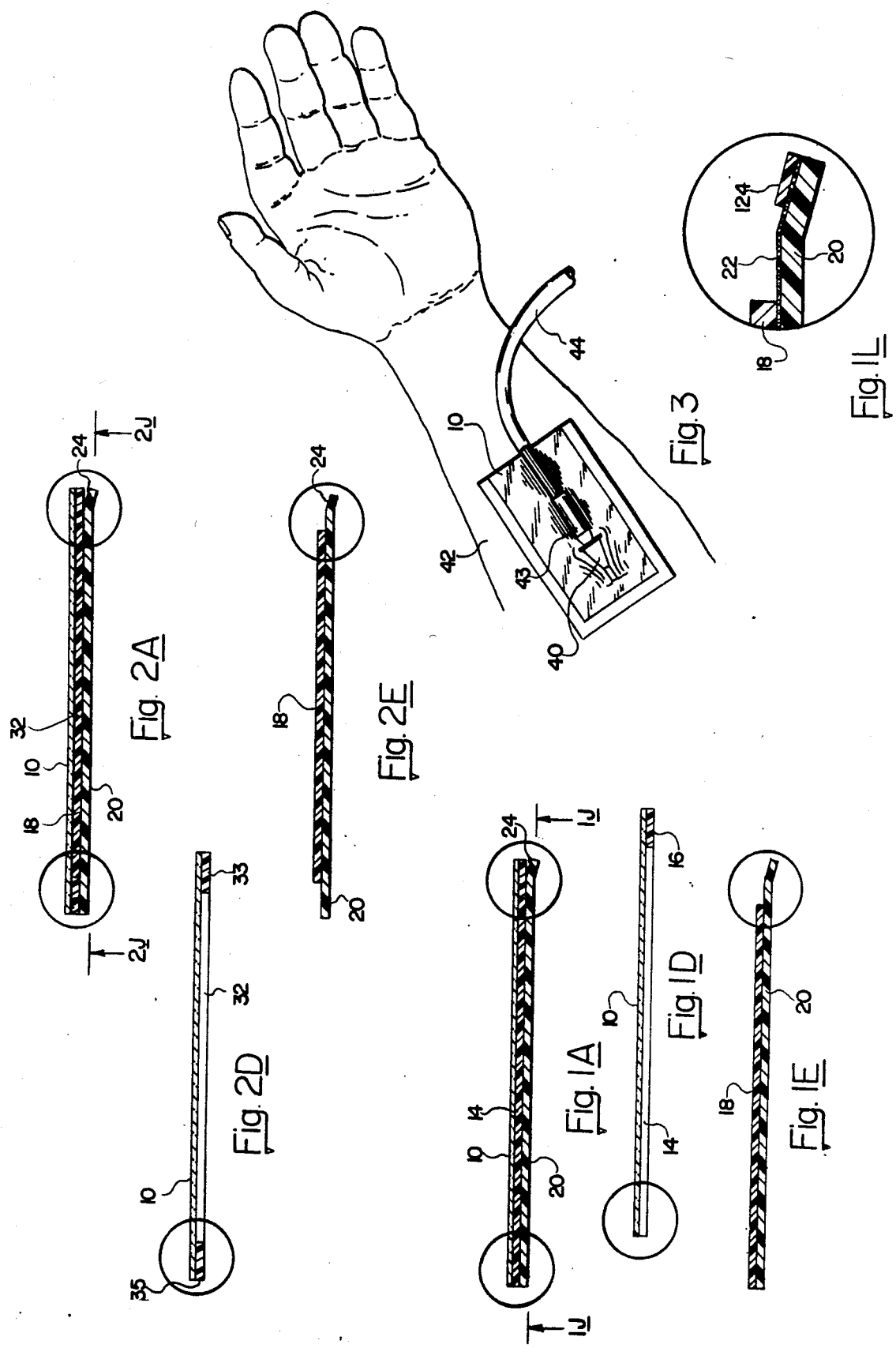

STERILE CATHETER SECUREMENT DEVICE

BACKGROUND OF THE INVENTION

1. Field of the Invention

With reference to the classification of art as established in and by the U. S. Patent Office, the present invention is believed to be found in the medical field and, more particularly, to a securing device for adhesively attaching and retaining a catheter and connected tubing for medication and/or fluids fed from an IV line into a catheter in a patient. This securement device is initially sterilized and with a protective and removable member when removed exposes an adhesively-coated and flexible plastic portion which is utilized for retention of the catheter and connected tubing to the skin of a patient.

2. Description of the Prior Art

The use of an adhesive coating on plastics, particularly thin and flexible plastic film, is very well known. Adhesive tape is and has been used with catheters and the securing of these members to the body parts of the patient being treated. Among U. S. patents of interest is No. 3,046,984 to EBY, as issued July 31, 1962. The retaining member is suggested to be of aluminum foil with an adhesive surface. Retention of a secondary conductor and needle is with a slot and viewing of the flow in the flexible tubing is through a rectangular opening. Also of note is U.S. Pat. No. 3,430,300, as issued to DOAN on Mar. 4, 1969. This patent shows a strip of flexible material with an adhesive surface and a release paper used therewith. The retention of a tube is with a loop formed around the tube and with extending wings of an aperture and wing members inserted through the aperture to secure the tube. Also noted is U.S. Pat. No. 3,918,446 to BUTTARAVOLI, as issued Nov. 11, 1975. This patent depicts a foldover device with appropriate cutouts for guiding the hookup connection and the tubing and to effect a retained and positioned placement. An additional adhesive is provided for securing the device to the skin of the patient. This device is for retaining the IV hookup to and into the vein or artery of a patient. This device does not show or suggest a thin, transparent plastic sheet with peripheral frames to permit ready removal from the added inserting site. BUTTARAVOLI also addressed this securement problem with another U.S. Patent, No. 4,324,237, as issued Apr. 13, 1982. Another U.S. Patent is No. 4,120,304 to MOOR, as issued Oct. 17, 1978, which shows an adhesive member of flexible material and an added clamp member of molded material.

Securing of catheters and connected tubing is also shown in other U.S. Patents, such as No. 3,574,306 to ALDEN, as issued Apr. 13, 1971; No. RE 27,519 to SHEPHERD et al, as issued Oct. 31, 1972; No. 3,973,565 to STEER, as issued Aug. 10, 1976; No. 4,059,105, as issued to CUTRUZZULA et al on Nov. 22, 1977; No. 4,149,534 to TENCZAR, as issued Apr. 17, 1979; No. 4,221,215 to MANDELBAUM, as issued Sept. 9, 1980; No. 4,390,105, as issued to CUMMINGS on June 28, 1983, and No. 4,534,762 to HEYER, as issued Aug. 13, 1985. The above-noted patented examples and other devices known to the Applicant do not teach or contemplate a securement device that has an additional protective member to maintain an initial sterilized condition through storage, shipment and until the attendant prior to immediate use removes this additional protective member to apply the securement device. The readied device is utilized by the attendant to hold a catheter and connected tubular member in position and to the prepped skin of the patient. This (these) release sheet(s) must be removed by the attendant from the securement device prior to use of the securement device.

In brief, and to be more fully described hereinafter, this invention is directed to overcoming these difficulties in providing an initially sterile retainer in which the exposed film is adhesively-coated and provides a securement of the placed catheter and a connected IV tubing and the like. The securement device is shown in two configurations. In a first embodiment, a frame portion is made with three sides and with a fourth side having no frame. In the other embodiment, the securement device has a four-edge frame. In both devices, a flexible film having one face coated with an adhesive is attached to the frame and also to a release sheet. Preferably the release sheet is die-cut as the frame is cut, with the cutout portion of the frame providing the release sheet which is not removed during assembly. This adhesively-coated film is adapted to be attached to the skin of the patient to retain the catheter and a tubular connection. An additional protective member of adhesively-coated film or paper is applied to fully cover the other side of the release sheet until used. One portion of this protective member covers the frame except for an outer portion which is absent adhesive or is covered to make a tab which provides means for insertion of a fingernail or the like. After assembly, the device is sterilized and, after sterilization, this protective member together with the adhesively-coated film provides and maintains internal sterility until time of application.

The skin of the patient is "prepped" for blood vessel puncture, then a catheter is inserted into the vein or artery of said patient. The protective cover of the securement device is removed by gripping the tab and adjacent frame, a one-step procedure. The securement device is ready for placement over the puncture site to secure the catheter and protect the catheter skin entrance site from contamination. The device of this application is shown in two embodiments and, in both, sterility is established and maintained until the protective member is removed just before application. The adhesive has been subjected to sterilization and has been selected from those which are acceptable for use on the human skin. This application is not directed to the composition of adhesive, per se, but to a simple-to-use, economical securement device for retaining a catheter and connected tubing in a substantially near-sterile condition.

SUMMARY OF THE INVENTION

This invention may be summarized, at least in part, with reference to its objects. it is an object of this invention to provide, and it does provide, a securement device utilizing a thin, transparent plastic film coated on one side with a substantially non-irritating adhesive having at least a partial border frame along three sides, with said frame portions on their exposed surfaces absent adhesive.

A further object of this invention is to provide, and it does provide, a one-step procedure for removing a sterile securement device from its package (protective film or paper) and ready for placement. Although the film is somewhat flimsy, the frame provides rigidity and ease of placement.

A further object of this invention is to provide, and it does provide, a securement device that is adaptable to automatic production equipment.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen two specific embodiments of a sterile catheter securement device as adopted for use in retaining a placed catheter and connector and showing a preferred means for construction, assembly and use. These specific embodiments have been chosen for the purposes of illustration and description as shown in the accompanying drawings wherein:

BRIEF DESCRIPTION OF THE DRAWINGS

FIG. 1 A represents a diagrammatic side view of the assembled sterile securement device;

FIG. 1 B represents a plan view of a three-sided frame with a supple film extending substantially to the edges of the frame, this view partly diagrammatic;

FIG. 1 C represents a plan view, partly diagrammatic, and showing a protective top cover and release sheet, with this protective cover having a tab portion devoid of adhesive, this cover adapted to be secured to the bottom film and frame to provide an assembly;

FIG. 1 D represents a side view of the bottom and frame, with a portion of the end of the frame shown in section, this view taken on the line 1 D—1 D of FIG. 1 B and looking in the direction of the arrows;

FIG. 1 E represents a sectional side view of the cover and release sheet, this view taken on the line 1 E—1 E of FIG. 1 C and looking in the direction of the arrows;

FIG. 1 F represents a fragmentary sectional side view in an enlarged scale of the end of assembly of FIG. 1 A including the attached tab portion;

FIG. 1 G represents a fragmentary sectional side view in an enlarged scale of the other end of the assembly of FIG. 1 A;

FIG. 1 H represents a fragmentary sectional side view in an enlarged scale of the end of the securement device as seen in FIG. 1 D;

FIG. 1 I represents a fragmentary sectional side view in an enlarged scale and showing an end portion of the cover member, release sheet and tab as depicted in FIG. 1 E;

FIG. 1 J represents a plan view of the securement device in an assembled condition as in FIG. 1 A;

FIG. 1 K represents the plan view of FIG. 1 J and showing the cover, release sheet and tab portion as these portions are peeled from in way of the frame and film;

FIG. 1 L represents a fragmentary sectional side view in an enlarged scale and showing the tab member as an additional layer of material attached to the adhesive coating on the top cover member;

FIG. 2 A represents a diagrammatic side view of the assembled sterile securement device;

FIG. 2 B represents a plan view of a four-sided frame with a supple film extending substantially to the edges of the frame, this view partly diagrammatic;

FIG. 2 C represents a plan view, partly diagrammatic, and showing the top cover, release sheet and tab member adapted to be secured to the bottom film and frame to provide an assembly;

FIG. 2 D represents a side view of the bottom and frame, with end portions of the frame shown in section, this view taken on the line 2 D—2 D of FIG. 2 B and looking in the direction of the arrows;

FIG. 2 E represents a sectional side view of the cover and release sheet, this view taken on the line 2 E—2 E of FIG. 2 C and looking in the direction of the arrows;

FIG. 2 F represents a fragmentary sectional side view in an enlarged scale of the end of assembly of FIG. 2 A including a film with an absence of adhesive to provide a tab portion;

FIG. 2 G represents a fragmentary sectional side view in an enlarged scale of the other end of the assembly of FIG. 2 A;

FIG. 2 H represents a fragmentary sectional side view in an enlarged scale of the end of the securement device as seen in FIG. 2 D;

FIG. 2 I represents a fragmentary sectional side view in an enlarged scale and showing an end portion of the cover member, release sheet and tab as depicted in FIG. 2 E;

FIG. 2 J represents a plan view of the securement device in an assembled condition as in FIG. 2 A;

FIG. 2 K represents the plan view of FIG. 2 J and showing the cover, release sheet and tab portions as these portions are peeled from in way of the frame and film, and FIG. 3 represents a diagrammatic plan view showing the securement device used to retain a catheter and connector to the skin of a patient.

In the following description and in the claims, various details are identified by specific names for convenience. These names are intended to be generic in their application. Corresponding reference characters refer to like members throughout the several figures of the drawings.

Figure 1F:
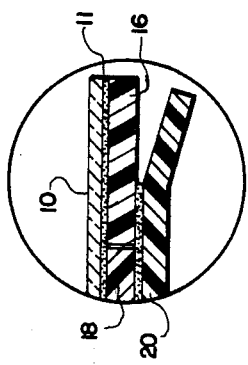
FIGS. 1 A through 1 K depict a sterile securement device in which a three-sided frame is provided.

The drawings accompanying, and forming part of, this specification disclose details of construction for the purpose of explanation, but structural details may be modified without departure from the concept and principles of the invention and the invention may be incorporated in other structural forms than shown.

EMBODIMENT OF FIGS. 1 A THROUGH 1 L

Referring next to the drawings and one of the embodiments shown in the drawings, there is depicted a sterile catheter securement device in which sterility is retained until just before application by an attendant. A bottom member 10 of film has an adhesive 11 applied to one surface of this film member. A frame member 12 is secured to this adhesive surface. This frame is of thin material which is preferably die-cut to shape. The material for the frame may be made of surgical grade kraft paper stock and have a thickness (such as a thickness of four- to ten-thousandths of an inch) or may be of plastic of a few thousandths of an inch in thickness. The bottom member 10 may be of polyurethane, vinyl or other plastic films that are supple and sufficiently flexible to conform to the skin of a patient. The adhesive 11 is a coating which may be an acrylate or other pressure-sensitive emulsion or melt adhesive which is non-irritating to the patient's skin. As reduced to practice, the film 10 is usually from one-half to four-thousandths of an inch in thickness, but this is a matter of selection, with consideration being made to the composition of film and adhesive. The adhesive coating is a commercial product and is usually from one-half to four-thousandths of an inch in thickness.

Figure 1G:
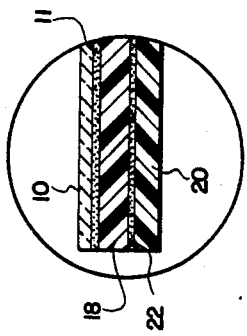
Figure 1H:
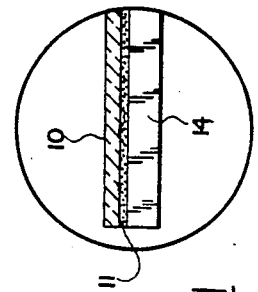
Figure 1J:
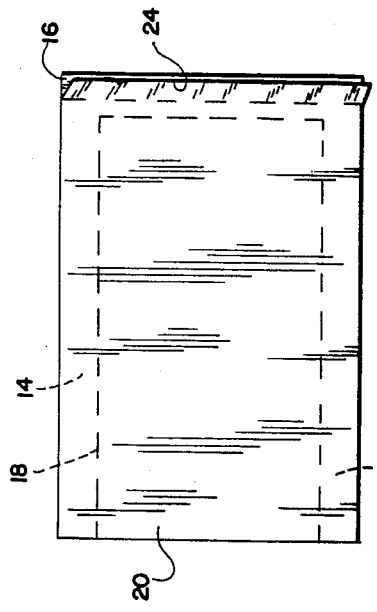
Figure 1K:
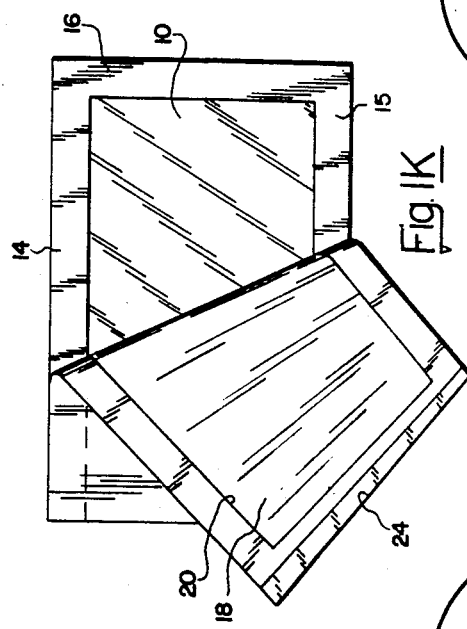
Figure 1I:
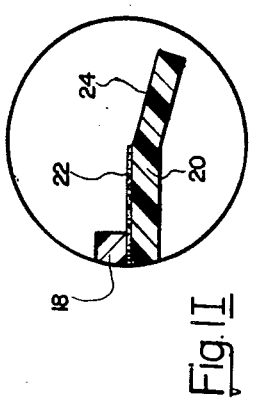
Figure 1B:
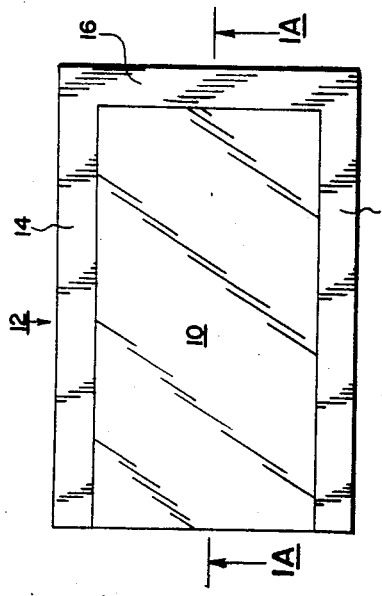
Figure 1C:
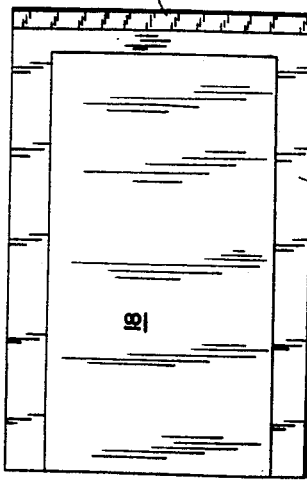

As seen in FIGS. 1 B and 1 D, the film 10 with the adhesive coating 11 and frame 12 are made the same size and are in coincidence. As depicted, the frame 12 is made with sides 14 and 15 of about one-quarter of an inch or less in width. An end portion 16 is provided with a similar or wider width, although these dimensions are merely a matter of choice. The extent of film interior of the frame portions 14, 15 and 16 has a release-sheet portion 18 which is adapted to substantially cover the film area interior of the frame. This release-sheet portion may be and usually is of the same material as provided for the frame 12. A protective sheet 20 is also provided. This protective sheet is usually of film or paper or, even if not, is intended to be impervious to passage therethrough of bacteria and the like.

As shown in FIGS. 1 C and 1 F, the protective cover 20 retains release sheet 18 in a desired position. An additional sealable material, which may be the cover itself or a coating on sheet 20, is conventionally provided to secure portion 18 to the cover 20. This surface, identified as 22, is at least sealably coated sufficiently to retain the cover member 20 to at least the frame portion adjacent the inner-edge portions of the frame. As shown in FIG. 1 I, the cover film 20 has the sealable material 22 stopped short of the end to provide a tab portion 24 that is absent a seal coating so that when the device is assembled this tab portion 24 lies adjacent and facing the end 16 of the frame 12. This tab portion 24 is thus void of a sealable coating.

In FIG. 1 L, an alternate tab structure is shown. The film 20, as conventionally provided in this embodiment, has a sealable coating 22 applied to all of one surface and a thin piece of paper or film, identified as 124, is secured to this sealable coating surface to render this portion ineffective and provide manipulating means for inserting a fingernail or the like between tab 24 (FIG. 1 I) or tab 124 (FIG. 1 L) and the frame portion 16 so as to grasp and lift the cover 20 and release sheet 18 from the securement member so that this film 10 may be used to secure a placed catheter.

When pulling the cover sheet from the securement device, a fiber tear bond or other discernible seal breakage becomes noticeable between the cover 20 and frame portions 14, 15 and 16. In this manner the user is assured the seal between the frame and cover was not tampered with previously. Any tampering of the supple film and release sheet surface results in film distortion such as creases or air pockets. Thus, until the time of use, it is quite difficult to disturb the seals without their being noticed.

USE AND OPERATION OF ASSEMBLY OF FIGS. 1 A THROUGH 1 L

The drawings particularly illustrate the assembly of the device and preparing the device for shipment, storage and use. This device is anticipated to be used mainly in the hospital and doctor's office where catheters are inserted into a patient. Sterility is important and desired where invasion of a patient's skin is present. This device is anticipated as being inexpensively produced from assembly to sterility procedures and use. By and with both the film 10 and adhesive 11 cut to size and shape by die means and with frame 12 also produced from sheet stock and die-cutting also contemplated, the aligning and assembly are by automatic, high-speed machinery. If desired, the release-sheet portion 18 may be placed in position at this time period and assembly procedure, with the release sheet 18 nearly filling the available space interior of the frame 10. The protector cover member 20, having a determined adhesive coating, is provided with a tab portion 24 which as a film portion absent a sealable coating provides means for insertion of a fingernail or the like (FIG. 1 I), or as an added member portion 124 is first secured and then this cover member assembly is placed and pressed into position as in FIG. 1 A.

It is to be noted that the sealable surface on cover member 20 extends at least partly over the separation of the frame and release sheet. The tab portion 24, although extending above the frame portion 16 as seen in FIG. 1 G, has the inner portion of cover member 20 securely attached to the frame 12. The cover 20 is sufficiently flexible to produce bending while making separation. Prior to shipping, the package as in FIG. 1 A is sterilized by a commercial and known method.

The sterile securing devices are grouped into stacks of like packages and sterilized. The cover 20 provides an inviolate barrier at the separation line interior of the frame 12 and the release sheet 18. After shipping, the packaged device is brought to the point of use. After placement of the catheter and hookup with a supply line, the patient's skin is prepped for securing the catheter in place. The device is as in FIG. 1 J, after which the cover 20 is removed. As seen in FIG. 1 K, tab 24, or tab 124 seen in FIG. 1 L, is grasped and cover 20 is peeled back from the frame 12. Since the release sheet is prepared for removal from the film 10 and its adhesive coating 11, it is anticipated that cover 20 and the release sheet 18 will be removed as a unit.

In the above-described securement device, FIG. 1 A shows a side view of an assembled product, with the left end of the product shown in an enlarged scale in FIG. 1 F. The other end of this assembled product is fragmentarily shown in the enlarged view of FIG. 1 G. The film 10 and frame 12 with adhesive 11 are shown in FIG. 1 D and an enlarged showing is fragmentarily illustrated in FIG. 1 H. The covering 20 and release sheet 18 with tab 24 secured thereto are shown in FIG. 1 C and in a side view in FIG. 1 E, with an enlarged fragmentary illustration provided in FIG. 1 E. FIG. 1 J shows the preferred construction of the device and FIG. 1 K shows a partial peeling of cover 20 from the frame 12 and film 10. FIG. 1 L shows an alternate tab construction.

EMBODIMENT OF FIGS. 2 A THROUGH 2 K

This embodiment is very like that of FIG. 1 A through 1 L, but the frame rather than three-sided is made as a four-sided member. It is, of course, realized that the fourth side may be made incomplete or with a portion of this fourth member severed or as two portions attached to the two longer side portions. Except for a change in the frame structure, this device is identical to or very near to the above-described device.

Figure 2F:
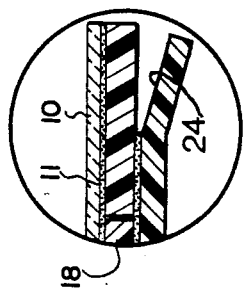
FIGS. 2 A through 2 K depict a sterile securement device in which a four-sided frame is provided.
Figure 2G:
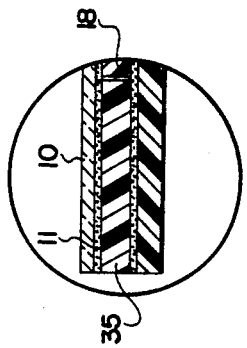
Figure 2H:
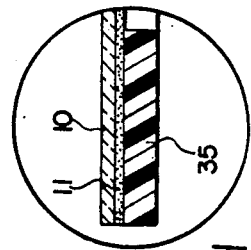
Figure 2J:
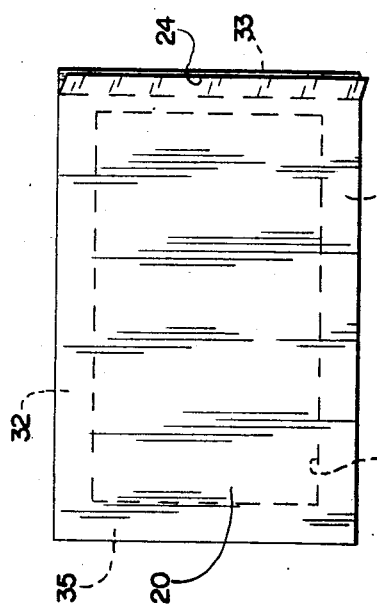
Figure 2K:
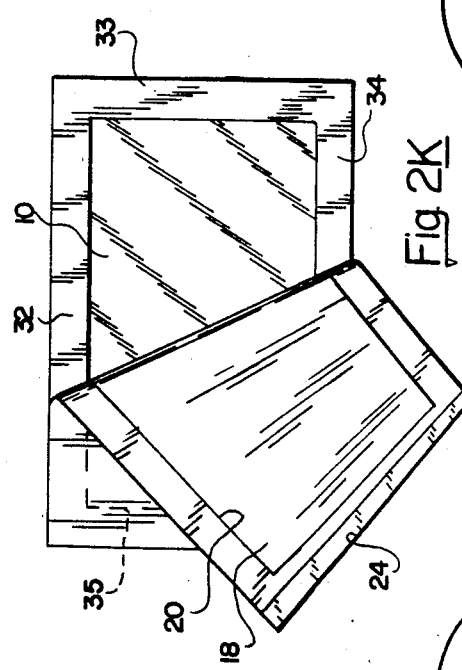
Figure 2I:
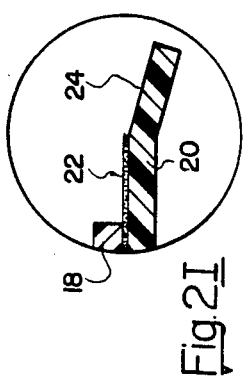
Figure 2B:
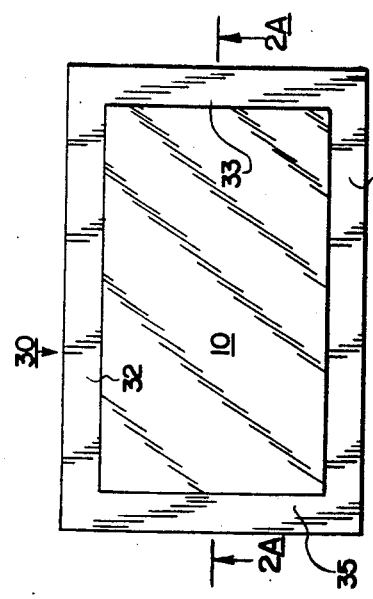
Figure 2C:
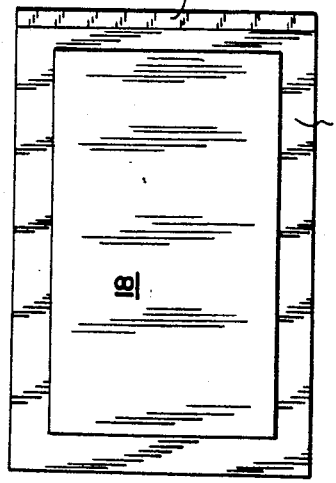

In FIGS. 2 A and 2 B, the film 10 and adhesive 11 are as identified above. A frame member 30 is depicted as having four outer closed portions 32, 33, 34 and 35 which are integrally secured and conventionally integral with the frame member made of sheet material. The release-sheet portion 18 is made of a size and configuration to fit within and extend substantially to the inner edge portions of said frame 30. The protective cover 20 is sized to extend substantially to the outer extents of the frame and a tab portion 24 of cover 20 or tab 124 is attached to said cover. The inwardly-directed surface of cover member 20 is also provided with a sealable surface 22 as above.

USE AND OPERATION OF EMBODIMENT OF FIGS. 2 A THROUGH 2 K

The assembly of the device of FIGS. 2 A through 2 K is substantially the same as for the device of FIGS. 1 A through 1 K above except that the frame has four outer portions. The assembly, sterilization and use are identical or very similar to that described above. It is to be noted in both devices that the release-sheet portion 18 is sufficiently flexible to permit a peeling action after the tab 24 is grasped and manipulated. This is particularly depicted in FIG. 2 K.

EMBODIMENT OF FIG. 3

In FIG. 3, the sterile catheter securing device is shown in use. The showing is with the device of FIG. 1 A in that the frame is three-sided. Whether with a frame with three sides or with a four-side arrangement as in FIG. 2 A, the sterile attachment device is brought to the site and in this view the protector 20, and the release sheet 18 have been removed to expose the adhesive surface of film 10. The site of the patient's skin has been prepped so as to bring the skin to the practical and lowest level of bacteria contamination. A catheter 40 is inserted into a patient 42 and a connecting end 43 of a conductor 44 is hooked up to said catheter. With the removal of protector 20 and release sheet 18, the adhesively-coated film 10 is positioned and tightly pressed to the skin of the patient to retain the catheter 40 and conductor 44 in the placed position. It is noted that the film 10 has been configured to tightly secure the connected portions. This adhesively-coated film provides (a) a bacteria barrier, (b) a securement device for securing the catheter and connecting tube to the patient's skin, and (c) by using a clear plastic film 10 provides a very visible window through which the catheter placement site during use may be observed.

It is to be noted that the frame 12, since it is absent any adhesive, may be used as a lift assist for removal of the securement device from the skin of the patient 42. The adhesive film 10 tightly secures the catheter 40 and connector tubing 44 and prevents contamination from the environment.

The cover film edge 24 is not coated. In this manner, a flap or tab is created which may be used for grasping and removal of the cover film with release sheet from the securement device. Tab 24 when of uncoated film, or tab 124 when of paper or like material added to the adhesive surface of the cover 20, may be thinner than the frame material. The tab 24 or 124 is shown as a full width, but this length is not required as tab extent need be only sufficient to allow a comfortable insertion of a fingernail between the frame and tab. Whether with a frame (three-sided) as in FIGS. 1 A through 1 L or the frame (four-sided) as in FIGS. 2 A through 2 K, the film 10 is contemplated to be sufficiently flexible so that with adhesive cementing 11 may be tightly pressed around the catheter 40 and tubular portion 44 where and when connected by the connected end 43. Whether a three-sided frame or a four-sided frame, the extent of adhesively-coated film 10 is sufficient to insure a retention of this connection. The frame provides an easy means for the attendant to remove the securement device after a determined period of time.

The sterile catheter securement device, although utilizing few components, is contemplated to be made in and with automatic high-speed apparatus. The resulting product, when assembled as in FIGS. 1 A or 2 A, contemplates a subsequent sterilizing procedure before final packaging for shipment. The resulting accumulation may be in a box-like retainer (not shown) in which a quantity such as fifty or one hundred, or some other selected quantity is packaged. As this product is conventionally used in a hospital, doctor's office or the like, with the catheter 40 inserted into the patient 42 and hooked up to the tubular conductor 44 in the usual manner, the surrounding skin area of the patient is now prepped. A securement device is now removed, one at a time, from the storage container and still in a sterile condition the tab portion 24 or 124 is manipulated in conjunction with an adjacent frame member and the cover 20 and release-sheet portion 18 are removed. Securing and use of this device in the desired mounted condition are depicted in FIG. 3.

The frame and release sheet are conventionally produced by a die-cutting operation and this representation in the drawings described above is as a line, with these two edges very contiguous. A very few thousandths of an inch spacing may occur at this die-cut, but when a peeling actuation is performed a separation of the frame and tab is easily achieved. The tab 24 or portion 124 is positioned at one end of the frame, which is a preferred location, but this is not to preclude placing the tab at the sides of the device. The tab 24 or a tab 124 is also shown as at or approximately at or in coincidence with the end of the frame, but this is also a matter of preference as long as the protector sheet 20 covers the inside of the frame and adjacent release sheet 14. This sheet protector insures that the adhesively-coated inside of the bottom film member 10 is kept inviolate until the device is used.

The frame and associated components as illustrated are depicted as rectangluar - which is easily and most economically produced by die-cutting, but it is to be understood that such showing is merely for the purpose of illustration. Other configurations - such as hexagonal, octagonal, oval and circular - are contemplated and may be provided within the scope of this invention. Shape and size is merely a matter of design and is not considered limiting.

The above invention as shown and described is believed to provide a basis for a method of constructing, assembling and using the sterile securement device for retaining an inserted and placed catheter and a connected tubular conductor to and from an IV supply and the like, this sterile securement device adapted for retaining and maintaining this assembled connection condition by an adhesively-coated film pressed to the skin of the patient, this method including the steps of:

providing a frame of sheet material having at least three outer-edge portions and establishing interior thereof and therebetween a determined space or area;

supplying a bottom film member which is sized to extend substantially to the outer edges or extents of said frame, this bottom film member very thin and flexible, and coating one surface of said bottom film member on one surface with an adhesive acceptable for contact attachment to the skin of a patient, and securing this film by this adhesive to said frame;

securing a flexible release sheet which is sized so as to extend to substantially the inner edges of the outer-edge portions of the frame, with this release sheet when in secured position protecting the adhesive surface of that bottom film interior of said frame-edge portions;

supplying and applying to said frame and said release sheet a protective sheet member of flexible composition and having a sealable material on one surface, said protective sheet member sized to extend substantially to the outer portions of said frame and enclose said release sheet, and supplying one edge of the protective sheet minus sealable means to form a tab member which provides means for separating the protective member from the frame and when said protective sheet member is sealably secured to the frame and release sheet, this protective sheet providing a covering of that space between the release sheet and frame-edge portions so that said spacing is protected from the environment, and after the protector is secured in place a sterilization of the assembled device is conventionally made.

Terms such as "left," "right," "up," "down," "bottom," "top," "front," "back," "in," "out" and the like are applicable to the embodiments shown and described in conjunction with the drawings. These terms are merely for the purposes of description and do not necessarily apply to the position in which the sterile catheter securement device may be constructed or used.

While particular embodiments of the securement device and initial construction and assembly have been shown and described, it is to be understood that the invention is not limited thereto and protection is sought to the broadest extent the prior art allows.

What is claimed is:

1. A sterile securement device for retaining an inserted and placed catheter and a connected tubular conductor to and from an IV supply and the like, this sterile securement device adapted for retaining and maintaining this assembled connection condition by an adhesively-coated film pressed to the skin of a patient, this sterile securement device including:
   (a) a frame of sheet material and providing at least three outer-edge, flat-surface portions and establishing interior thereof and therebetween a determined space or area;
   (b) a bottom thin and flexible film member sized to extend substantially to the outer extents of said frame, this film coated on one surface with an adhesive acceptable for contact attachment to the skin of a patient, this film with the adhesively-coated side secured to the flat-surface portions of the frame;
   (c) a flexible release sheet sized to extend to the inner edges of the frame and secured to said flat-surface portions of the frame, with the bottom thin and flexible film protecting the adhesive surface of that bottom film interior of said frame-edge, flat-surface portions;
   (d) a protector sheet member of flexible composition and having an adhesive capability of one surface, this protective sheet member sized to extend substantially to the outer edges of said frame, and with said device in an assembled condition this protector sheet is adhesively secured to an outer surface of the frame and flexible release sheet, and
   (e) a tab section not secured to said frame, this tab providing means for gripping and separating the frame from the protective sheet, and when said protector member is secured to said frame and release sheet, this protector sheet member covers that space between the release sheet and frame so that this spacing is protected from the environment, and after this protector is secured in place a sterilization of device is conventionally made.

2. A sterile securement device as in claim 1 in which the frame is of surgical grade paper having a thickness of ten thousandths of an inch or less and is die-cut to provide integral outer portions.

3. A sterile securement device as in claim 2 in which the frame is U-shaped with two side-edge members and a transverse connecting portion, and the tab member is facing this end portion and is adjacent thereto.

4. A sterile securement device as in claim 1 in which the frame is of plastic having a thickness of ten thousandths of an inch or less.

5. A sterile securement device as in claim 4 in which the frame is U-shaped with two side-edge members and a transverse connecting end portion, and the tab member is facing this end portion and is adjacent thereto.

6. A sterile securement device as in claim 1 in which the bottom film member is of polyurethane and is of five mils or less in thickness.

7. A sterile securement device as in claim 6 in which the adhesive surface portion applied to the bottom film is four mils or less in thickness.

8. A sterile securement device as in claim 1 in which the frame and release sheet are die-cut from the same strip of material.

9. A sterile securement device as in claim 1 in which the protector member is from a flexible plastic strip and the adhesive coating applied thereto adapted to retain the release sheet during and after manipulative peeling of the release sheet from the adhesive surface of the bottom film member.

10. A sterile securement device as in claim 1 in which the protector member is from a flexible strip of paper and the adhesive coating applied thereto adapted to retain the release sheet during and after manipulative peeling of the release sheet from the adhesive surface of the bottom film member.

11. A sterile securement device as in claim 1 in which the frame and release sheet are of surgical grade paper and are die-cut to produce a frame of two side- and two end-edge portions integrally connected and the release-sheet portion is from this residual central portion.

12. A sterile securement device as in claim 1 in which the protector sheet member is of an extent so as to extend to or substantially to the outer extent of the frame edge portions, with the tab portion sized and positioned to extend outward of that space between the release sheet and frame-edge portion, said tab member being a sheet-like member.

13. A sterile securement device as in claim 12 in which the frame, the bottom film member and the protector sheet member are made in a substantially rectangular planar configuration, with the bottom film member and protector member substantially the same configuration.

14. A sterile securement device as in claim 12 in which the tab member secured to the adhesive surface of the protector sheet member lies adjacent an end member of the frame and outward of the inner edge of an end outer-edge portion of the frame.

15. A sterile securement device as in claim 14 in which the tab member is of a thinner thickness than the protective member.

16. A sterile securement device as in claim 12 in which the tab member which is secured to the adhesive surface of the protector sheet member lies adjacent a side-edge portion and outward of the inner edge of a side-edge portion of the frame.

17. A sterile securement device as in claim 12 in which the tab member is of a width which is less than the length of the edge portion of the frame to which it is adjacent.

18. A sterile securement device as in claim 1 in which the protector sheet member is of paper or the like.

19. A sterile securement device as in claim 1 in which the protector sheet member is of an extent so as to extend to or substantially to the outer extents of the frame-edge portions, this protector member having the adhesive capability surface as an adhesive coating extending over the entire inwardly-facing surface, and the tab member is a thin strip of paper or like material secured to this adhesive surface to render this surface portion at the tab-member portion ineffective and provide means for the insertion of a fingernail or the like for manipulative removal of the protective member.

20. A sterile securement device for retaining an inserted and placed catheter and a connected tubular conductor to and from an IV supply and the like, this sterile securement device adapted for retaining and maintaining this assembled connection condition by an adhesively-coated film pressed to the skin of a patient, this sterile securement device including:
  (a) a frame of sheet material and providing at least three outer-edge, flat-surface portions and establishing interior thereof and therebetween a determined space or area;
  (b) a bottom thin and flexible film member sized to extend substantially to the outer extents of said frame, this film coated on one surface with an adhesive acceptable for contact attachment to the skin of a patient, this film with the adhesively-coated side secured to the flat-surface portions of the frame;
  (c) a flexible release sheet sized to extend to the inner edges of the frame and secured to said flat-surface portions of the frame, with the bottom thin and flexible film protecting the adhesive surface of that bottom film interior of said frame-edge, flat-surface portions, said frame and flexible release sheet produced by die-cutting from the same strip of material, with the space between the inside of the frame and the outer edge of the release sheet substantially contiguous;
  (d) a protector sheet member of flexible composition and having an adhesive capability of one surface, this protective sheet member sized to extend substantially to the outer edges of said frame, and with said device in an assembled condition this protector sheet is adhesively secured to an outer surface of the frame and flexible release sheet, and
  (e) a tab portion extending beyond the determined extent of adhesive surface of the protective member, said tab providing means for separating the protector member from the frame, and when said protector member is secured to said frame and release sheet, this protector sheet member covers that space between the release sheet and frame so that this spacing is protected from the environment, and after this protector is secured in place a sterilization of device is conventionally made.

21. A sterile securement device as in claim 20 in which the tab portion is provided by stopping the adhesive capability short of an edge of the protective member so that this cover portion absent adhesive capability is adapted to lie against the frame without securement.

22. A sterile securement device as in claim 21 in which the tab portion includes providing an adhesive coating so as to extend over the entire inwardly-facing surface, and the tab member is a thin strip of paper or like material secured to this adhesive surface to render this adhesive portion at the tab member portion ineffective and provide means for the insertion of a fingernail or the like for manipulative removal of the protective member.

23. A sterile securement device as in claim 22 in which the tab portion is made from very thin paper.

24. A method for constructing, assembling and applying a sterile securement device for retaining an inserted and placed catheter and a connected tubular conductor to and from an I.V. supply and the like, this sterile securement device adapted for retaining and maintaining this assembled connection condition by a breathable, adhesively-coated film pressed to the skin of the patient, this method including the steps of:
  (a) providing a frame of sheet material having at least three outer-edge portions and establishing interior thereof and therebetween a determined space or area;
  (b) supplying a bottom film member which is sized to extend substantially to the outer edges or extents of said frame, this bottom film member very thin and flexible, and coating one surface of said bottom film member on one surface with an adhesive acceptable for contact attachment to the skin of a patient, and securing this film by this adhesive to said frame;
  (c) securing a flexible release sheet which is sized so as to extend to substantially the inner edges of the outer-edge portions of the frame, with this release sheet when in secured position protecting the adhesive surface of that bottom film interior of said frame-edge portions;
  (d) supplying and applying to said frame a protective sheet member of flexible composition and having a sealable material on one surface, said protective sheet member sized to extend substantially to the outer portions of said frame, and
  (e) supplying one edge of the protective sheet minus sealable means to form a tab member which provides means for separating the protective member from the frame and, when said protective sheet member is sealably secured to the frame and release sheet, this protective sheet providing a covering of that space between the release sheet and frame-edge portions so that said spacing is protected from the environment, and after the protector is secured in place a sterilization of the assembled device is conventionally made.

25. A method for constructing, assembling and applying a sterile securement device as in claim 24 which includes the further step of forming the frame and release sheet from the same strip of material by a die-cutting procedure and apparatus.

26. A method of constructing, assembling and applying a sterile securement device as in claim 25 in which the frame and release-sheet strip of material are surgical grade paper.

27. A method of constructing, assembling and applying a sterile securement device as in claim 26 in which the produced frame includes forming the frame with two side- and two end-edge portions and integrally connecting said portions to adjacent edge portions.

28. A method of constructing, assembling and applying a sterile securement device as in claim 24 in which the frame and release-sheet strip material is of plastic.

29. A method of constructing, assembling and applying a sterile securement device as in claim 28 in which the produced frame includes forming the frame with two side- and two end-edge portions and integrally connecting said portions to adjacent edge portions.

30. A method of constructing, assembling and applying a sterile securement device as in claim 24 which further includes extending an adhesive on the protective member so that a tab strip may be secured to this adhesive as an added strip; this securing of the tab member to the protective member is positioned so that said tab lies adjacent to an end member of the frame and outward of the inner edge of an end outer-edge portion of the frame.

31. A method of constructing, assembling and applying a sterile securement device as in claim 24 which further includes extending an adhesive on the protective member so that a tab strip may be secured to this adhesive as an added strip; this securing of the tab member to the protective member is positioned so that said tab lies adjacent a side-edge member of the frame and outward of the inner edge of an outer side-edge portion of the frame.

32. A method of constructing, assembling and applying a sterile securement device as in claim 24 which includes forming the protective sheet member of paper, and the tab member of a thickness different from the protective sheet member.

33. A method of constructing, assembling and applying a sterile securement device as in claim 24 which further includes providing the tab portion on the protective member by terminating the application of an adhesive coating to the protective member so that this portion absent an adhesive coating is void of adhesive attraction to the frame.

34. A method of constructing, assembling and applying a sterile securement device as in claim 33 which further includes providing and positioning said tab portion so as to lie adjacent the end-member portion of said frme and outward of the inner edge of said frame.

* * * * *